(12) United States Patent
Wang et al.

(10) Patent No.: US 12,295,742 B2
(45) Date of Patent: May 13, 2025

(54) PHOTOACOUSTIC NEAR-INFRARED SPECTROSCOPIC ENDOSCOPY

(71) Applicants: Lihong Wang, Pasadena, CA (US); Konstantin Maslov, Pasadena, CA (US); Methodius Tuuli, St. Louis, MO (US); Molly Stout, St. Louis, MO (US); George Macones, St. Louis, MO (US); Junhui Shi, Pasadena, CA (US); Peinan Zhao, St. Louis, MO (US); Yuan Qu, St. Louis, MO (US); Peng Hu, St. Louis, MO (US)

(72) Inventors: Lihong Wang, Pasadena, CA (US); Konstantin Maslov, Pasadena, CA (US); Methodius Tuuli, St. Louis, MO (US); Molly Stout, St. Louis, MO (US); George Macones, St. Louis, MO (US); Junhui Shi, Pasadena, CA (US); Peinan Zhao, St. Louis, MO (US); Yuan Qu, St. Louis, MO (US); Peng Hu, St. Louis, MO (US)

(73) Assignees: Washington University, St. Louis, MO (US); California Institute of Technology, Pasadena, CA (US)

( * ) Notice: Subject to any disclaimer, the term of this patent is extended or adjusted under 35 U.S.C. 154(b) by 210 days.

(21) Appl. No.: 17/110,824

(22) Filed: Dec. 3, 2020

(65) Prior Publication Data
US 2021/0169414 A1    Jun. 10, 2021

Related U.S. Application Data

(60) Provisional application No. 62/944,333, filed on Dec. 5, 2019.

(51) Int. Cl.
A61B 5/00 (2006.01)
A61B 1/00 (2006.01)
(Continued)

(52) U.S. Cl.
CPC ........ *A61B 5/4875* (2013.01); *A61B 1/00096* (2013.01); *A61B 1/0638* (2013.01);
(Continued)

(58) Field of Classification Search
CPC . A61B 5/4875; A61B 1/00096; A61B 1/0638; A61B 1/07; A61B 5/0095; A61B 1/00172; A61B 5/0084; A61B 5/435
See application file for complete search history.

(56) References Cited

U.S. PATENT DOCUMENTS 7,515,948 B1    4/2009  Balburg
8,180,419 B2    5/2012  Debreczeny
(Continued)

FOREIGN PATENT DOCUMENTS

CN    107713993    3/2019

OTHER PUBLICATIONS

Yang J. et al. (2009) Photoacoustic endoscopy. Opt. Lett., vol. 34, p. 1591-1593.
(Continued)

*Primary Examiner* — Baisakhi Roy
*Assistant Examiner* — Kaitlyn E Sebastian

(57) ABSTRACT

In various aspects, a photoacoustic endoscopic probe and methods for measuring a hydration of a connective tissue in vivo using the photoacoustic endoscopic probe are disclosed.

8 Claims, 6 Drawing Sheets

(51) Int. Cl.
*A61B 1/06* (2006.01)
*A61B 1/07* (2006.01)

(52) U.S. Cl.
CPC .............. *A61B 1/07* (2013.01); *A61B 5/0095* (2013.01); *A61B 1/00172* (2013.01)

(56) References Cited

U.S. PATENT DOCUMENTS

| | | | | |
|---|---|---|---|---|
| 2002/0183602 | A1* | 12/2002 | Wenzel | G01N 21/4785 600/473 |
| 2010/0268058 | A1* | 10/2010 | Chen | A61B 8/4483 600/407 |
| 2015/0005613 | A1* | 1/2015 | Kim | G01N 29/2418 600/407 |
| 2016/0235305 | A1* | 8/2016 | Wang | A61B 5/0873 |
| 2019/0159705 | A1* | 5/2019 | Sim | A61B 5/14532 |
| 2019/0219831 | A1* | 7/2019 | Duckett | A61B 1/042 |

OTHER PUBLICATIONS

Yang J. et al. (2012) Simultaneous functional photoacoustic and ultrasonic endoscopy of internal organs in vivo. Nat. Med., vol. 18, p. 1297-1302.
Yang J. et al. (2012) A 2.5-mm diameter probe for photoacoustic and ultrasonic endoscopy. Opt. Express, vol. 20, p. 23944-23953.
Yang J. et al. (2014) "Catheter-based photoacoustic endoscope," J. Biomed. Opt., vol. 19, p. 066001.
Li C. et al. (2014) Urogenital photoacoustic endoscope. Opt. Lett., vol. 39, p. 1473-1476 (2014).
Yang J. et al. (2015) Optical-resolution photoacoustic endomicroscopy in vivo. Biomed. Opt. Express, vol. 6, p. 918-932.
Wilson R. H. et al. (2015) Review of short-wave infrared spectroscopy and imaging methods for biological tissue characterization. J. Biomed. Opt., vol. 20, p. 030901.
Li L. et al. (2016) Label-free photoacoustic tomography of whole mouse brain structures ex vivo. Neurophotonics, vol. 3, p. 035001.
Li L. et al. (2017) Single-impulse panoramic photoacoustic computed tomography of small-animal whole-body dynamics at high spatiotemporal resolution. Nat. Biomed. Eng., vol. 1, p. 0071.
Li L. et al. (2017) Multiview Hilbert transformation in full-ring transducer array-based photoacoustic computed tomography. J. Biomed. Opt., vol. 22, 076017 (2017).

* cited by examiner

PHOTOACOUSTIC NEAR-INFRARED SPECTROSCOPIC ENDOSCOPY

CROSS-REFERENCE TO RELATED APPLICATIONS

This application claims priority from U.S. Provisional Application Ser. No. 62/944,333 filed on Dec. 5, 2019, which is incorporated herein by reference in its entirety.

STATEMENT REGARDING FEDERALLY SPONSORED RESEARCH OR DEVELOPMENT

This invention was made with government support under EB016986 and CA186567 awarded by the National Institutes of Health. The government has certain rights in the invention.

FIELD OF THE DISCLOSURE

The present disclosure generally relates to methods of characterizing connective tissue remodeling using infrared photoacoustic spectra.

BACKGROUND OF THE DISCLOSURE

The cervix is a remarkable structure with diametrically opposite functions: it maintains pregnancy by remaining closed and then, in a process called remodeling, softens and dilates to allow delivery of the fetus in labor. Premature cervical remodeling is a critical indicator of impending spontaneous preterm birth. Preterm birth can occur with a remodeled cervix even in the absence of uterine contractions, but uterine contractions do not lead to delivery if the cervix is firm. Nevertheless, current clinical measurements of cervical remodeling are largely obtained by digital examinations, which are subjective and detect only late events, such as cervical effacement and dilation.

The cervix remodels progressively via incompletely under-stood mechanisms, such as degradation of extracellular matrix proteins and inflammation. These physiological changes are associated with increased tissue hydration. Therefore, a method that can accurately measure cervical hydration during pregnancy has the potential to facilitate current understanding of cervical remodeling and permit more accurate prediction of preterm birth.

Near-infrared spectroscopy is routinely used in industrial applications to quantify the water content in various products, because this method is nondestructive and does not require sample preparation. As an embodiment of near-infrared spectroscopy, spectroscopic photoacoustic tomography has been demonstrated in the quantification of various biochemical constituents. However, the previous applications used tabletop systems, which precluded in vivo use in the gastrointestinal tract and urogenital tract. Photoacoustic endoscopy (PAE) incorporates an acoustic detector, optical components, and electronic components in a millimeter-diameter-scale probe to image tissue that is inaccessible by tabletop systems.

For the quantification of the water content of the cervix in a pregnant woman, the combination of PAE and near-infrared spectroscopy provides an optimal solution. However, the task is nontrivial, because PAE needs an acoustic coupling medium, which generally contains water as well. The photoacoustic signals emitted by the acoustic coupling medium are not easily separable from the signals emitted by the tissue in the near-infra-red wavelength range. This challenge so far has precluded the use of near-infrared spectroscopic PAE for the quantification of water content.

Premature cervical remodeling is a critical precursor of spontaneous preterm birth, and the remodeling process is characterized by an increase in tissue hydration. Nevertheless, current clinical measurements of cervical remodeling are subjective and detect only late events, such as cervical effacement and dilation.

SUMMARY OF THE DISCLOSURE

In one aspect, a photoacoustic endoscopic probe for obtaining photoacoustic near-infrared spectra from a region of interest is disclosed that includes a beam combiner configured to direct light energy received from a light source into the region of interest and further configured to direct photoacoustic signals generated by at least one structure within the region of interest to an acoustic detector. The photoacoustic signals are produced within the region of interest in response to illumination by the light energy.

In another aspect, a method for measuring a hydration of a connective tissue in vivo using a photoacoustic endoscopic probe is disclosed. The method includes providing the endoscopic probe. The endoscopic probe includes a beam combiner configured to direct light energy received from a light source into a region of interest containing the connective tissue and further configured to direct photoacoustic signals generated by the connective tissue within the region of interest to an acoustic detector. The method also includes directing the light produced by the light source into the region of interest using the endoscopic probe. The light is produced in a wavelength scanning pattern ranging from a minimum wavelength to a maximum wavelength. The method further includes detecting the photoacoustic signals produced within the region of interest in response to illumination by the light and transforming the detected photoacoustic signals into a photoacoustic spectrum. The photoacoustic spectrum includes a plurality of photoacoustic signals and a corresponding wavelength. The corresponding wavelength is indicative of the wavelength of light used to produce the corresponding photoacoustic signal. The method further includes transforming the photoacoustic spectrum into a tissue hydration using at least one predetermined single wavelength linear regression model.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

Figure 1A:
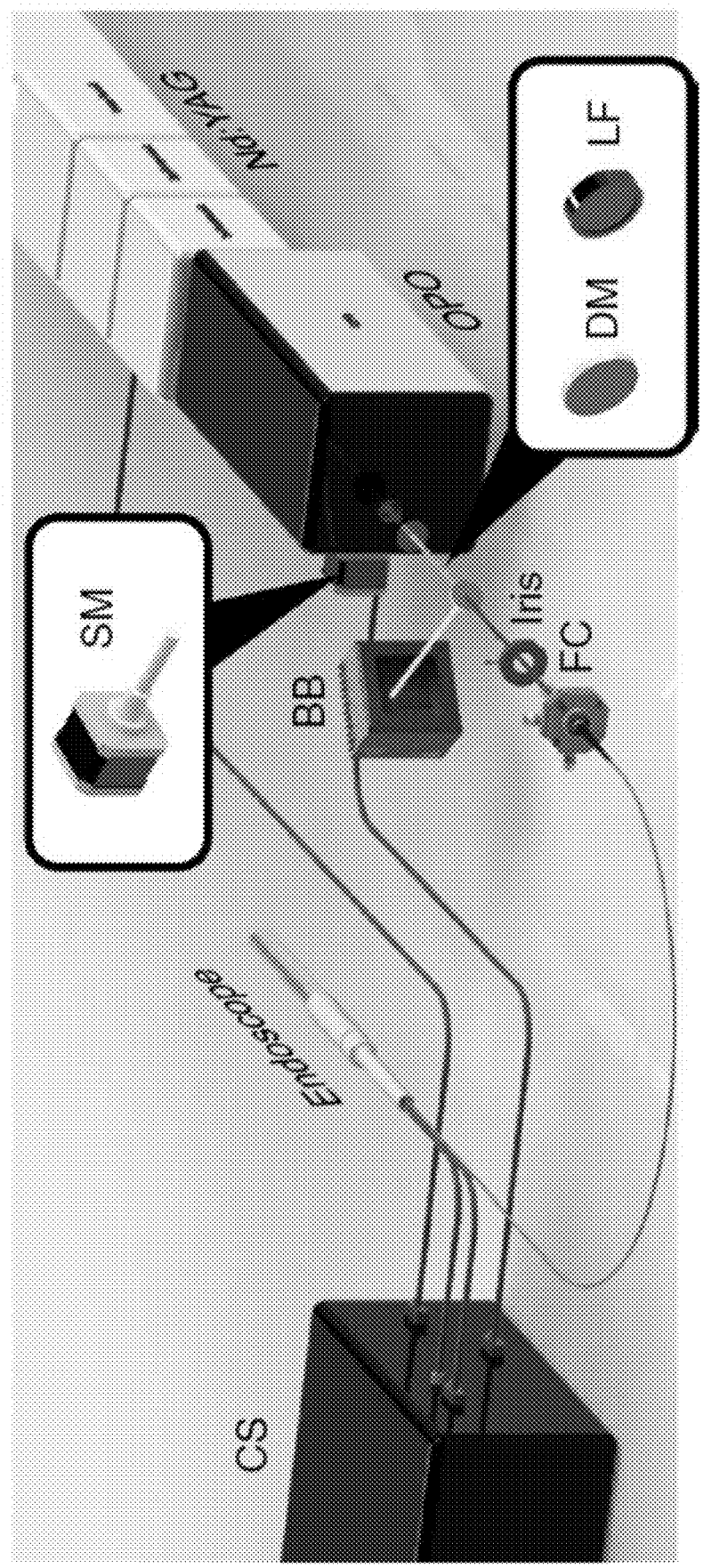
FIG. 1A is a schematic diagram illustrating the elements of a photoacoustic near-infrared (PANIR) system in accordance with one aspect of the disclosure. PANIR system elements include: BB, beam block; CS, control system; DM, dichroic mirror; FC, fiber coupler; LF, longpass filter; Nd:YAG, Nd:YAG laser with a frequency tripling module; OPO, optical parametric oscillator; and SM, stepper motor.

There are shown in the drawings arrangements, which are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION OF THE INVENTION

In various aspects, a photoacoustic endoscope device configured to measure near-infrared spectra non-invasively from viscera and methods of quantifying tissue hydration by transforming the near-infrared spectra obtained by the photoacoustic endoscope. The disclosed device and methods enable the quantification of tissue hydration in vivo without invasive biopsies associated with existing methods of quantifying tissue hydration in vivo.

In various aspects, an in vivo PANIR endoscopy system is described that measures the cervical PANIR spectra of pregnant women. The PANIR system enables the detection of serial and cross-sectional changes in PANIR spectra obtained from cervical connective tissues of pregnant women. In various other aspects, the PANIR spectra are transformed into a quantification of cervical hydration using single-wavelength linear regression models, enabling the non-invasive monitoring of cervical hydration during pregnancy. As described in the examples below, cervical hydration estimated from in vivo PANIR endoscopy system measurements is consistent with previously published values. Measurement of PANIR spectra and the cervical hydration levels using the disclosed PANIR endoscopy system introduces new possibilities for studying preterm birth. By way of non-limiting example, longitudinal monitoring of cervical hydration using the disclosed systems and method may potentially elucidate the influence of environmental or patient-specific factors on the risk of preterm birth.

In one aspect, a near-infrared spectroscopic photoacoustic endoscopy (PAE) system that transmits acoustic waves from the tissue to the acoustic detector through an N-BK7 pentaprism is disclosed. In another aspect, a method of transforming photoacoustic near-infrared (PANIR) spectra measured by the disclosed system into quantifications of tissue hydration using linear regression is disclosed. As described in additional detail below, the disclosed method was validated by quantifying the water contents of tissue-mimicking phantoms made of gelatin hydrogel.

In various aspects, the combination of photoacoustic endoscopy and near-infrared spectroscopy enables the quantification of the water content of the cervix in pregnant women. However, this quantification is nontrivial, because photoacoustic endoscopy needs an acoustic coupling medium, which generally contains water, to ensure impedance-matched acoustic coupling between the cervix and the endoscope containing the acoustic transducer used to detect photoacoustic signals. In addition, the photoacoustic signals emitted by the acoustic coupling medium are not easily separable from the signals emitted by the tissue in the near-infra-red wavelength range. This challenge so far has precluded the use of near-infrared spectroscopic PAE for the quantification of water content in vivo.

I. PANIR System

A photoacoustic near-infrared (PANIR) system is shown illustrated in FIG. 1A. The system is controlled by a custom-designed program written in LabVIEW (National Instruments). A frequency-tripled Nd:YAG laser (Quantel, Q-smart 450), operating at 355-nm wavelength with a 20-Hz pulse repetition rate, pumps an optical parametric oscillator (GWU-Lasertechnik, basiScan). A stepper motor moves the optical parametric oscillator so that the idler light can be scanned from 1000 to 2000 nm. After passing through the oscillator, the remaining energy of the pump light is absorbed by a longpass filter. The idler light is selected by a dichroic mirror and then coupled into a multimode fiber, which guides the light to the PANIR probe, shown illustrated in FIG. 1B. Referring again to FIG. 1A, an iris between the dichroic mirror and the fiber coupler controls the delivered optical energy, keeping the optical fluence (mJ/cm$^2$) delivered to the tissue surface below the American National Standards Institute safe exposure limit.

The methods and algorithms disclosed herein may be enclosed in a controller or processor. Furthermore, methods and algorithms disclosed herein can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Embodiments of the disclosure may be described in the general context of computer-executable instructions, such as program modules, executed by one or more computers or other devices. The computer executable instructions may be organized into one or more computer executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer executable instructions or components having more or less functionality than illustrated and described herein. Aspects of the disclosure may also be practiced in distributed computing environments where tasks are performed by remote processing devices that are linked through a communications network. In a distributed computing environment, program modules may be located in both local and remote computer storage media including memory storage devices.

The computer systems, computing devices, and computer implemented methods discussed herein may include additional, less, or alternate actions and/or functionalities, including those discussed elsewhere herein. The computer systems may include or be implemented via computer executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function which maps outputs to inputs and utilize the predictive function to generate ML outputs based on data inputs. The example inputs and example outputs of the training data may include any of the data inputs or ML outputs described above. For example, a ML module may receive training data comprising customer identification and geographic information and an associated customer category, generate a model which maps customer categories to customer identification and geographic information, and generate a ML output comprising a customer category for subsequently received data inputs including customer identification and geographic information.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship. In one aspect, a ML module receives unlabeled data comprising customer purchase information, customer mobile device information, and customer geolocation information, and the ML module employs an unsupervised learning method such as "clustering" to identify patterns and organize the unlabeled data into meaningful groups. The newly organized data may be used, for example, to extract further information about a customer's spending habits.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, a ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

II. PANIR Probe

Figure 1B:
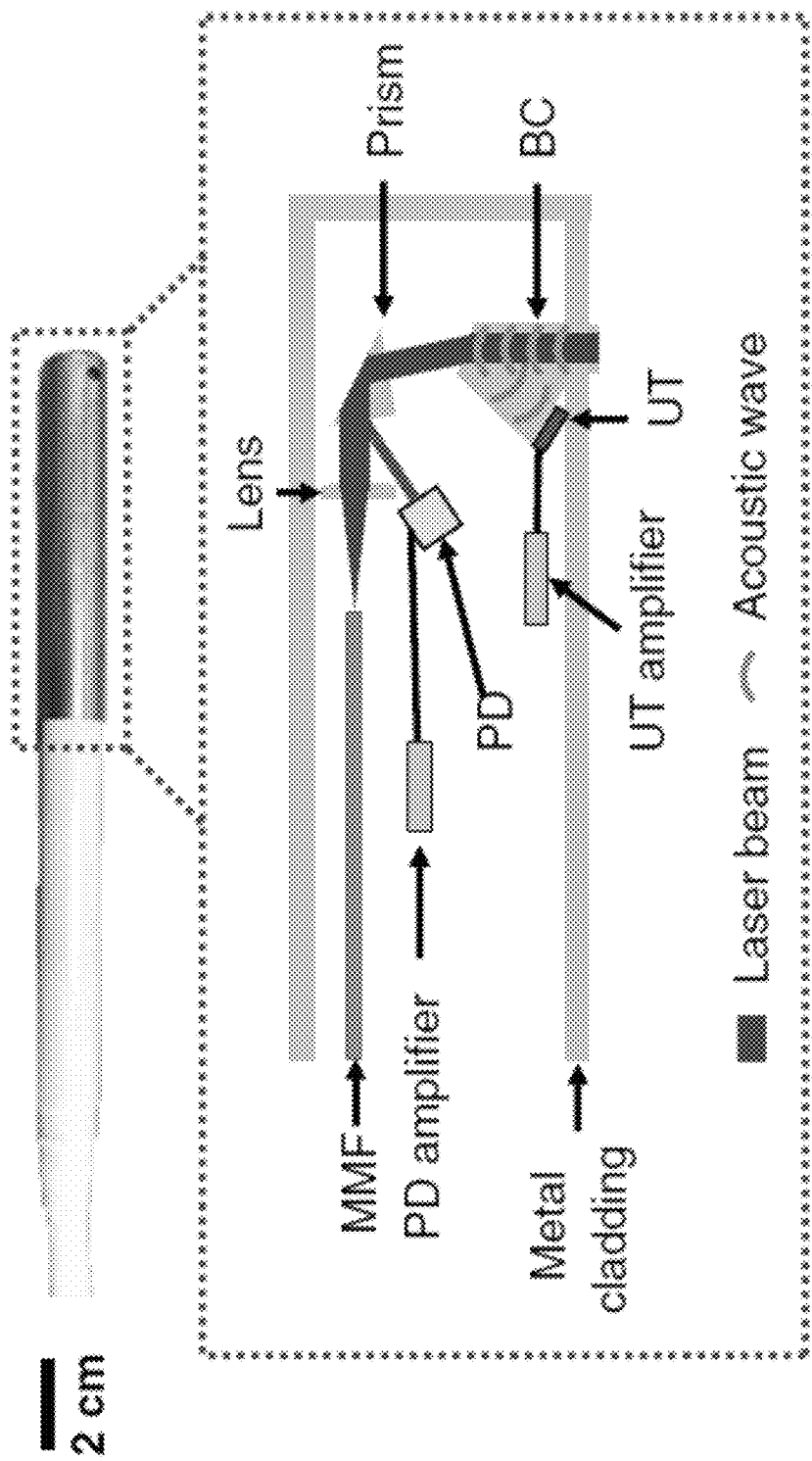
FIG. 1B is an image of a PANIR endoscope probe (top) and a schematic diagram (bottom) illustrating the elements of the PANIR endoscope probe in accordance with one aspect of the disclosure. The PANIR endoscope probe elements include: BC, beam combiner; MMF, multimode fiber; PD, calibrated photodiode; and UT, ultrasonic transducer.

The internal structure of the PANIR probe, which is 30 cm in the length and 2 cm in the diameter, is shown illustrated in FIG. 1B. The idler light from the multimode fiber is projected onto the tissue surface by a plano-convex lens and a prism and is absorbed by the tissue below the optical-acoustic beam combiner—a custom-designed pentaprism. The backward photoacoustic wave propagates through the beam combiner and is directed toward an ultrasonic transducer (2.25-MHz central frequency) configured to detect the photoacoustic wave. The configuration of the optical and acoustic elements reduces the amount of light absorbed by the ultrasonic transducer to a negligible level. While the idler light is sweeping over the entire spectral range, the detected photoacoustic signal is overwhelmed by noise only when air is underneath the beam combiner. The InGaAs photodiode (FD10D, Thorlabs) in the probe continually measures the energy of the idler light to correct for its energy fluctuations in subsequent data processing. In some aspects, the PANIR system may be calibrated periodically with graphite to correct for instrument drift.

In various additional aspects, the PANIR spectra may be transformed into quantifications of tissue hydration using comprehensive machine learning models, which may reveal other phenomena latent within the PANIR spectra beyond human perception.

EXAMPLES

The following examples are provided to describe various aspects of the disclosure.

Example 1: Quantification of Water Content in Hydrogel Phantoms

To validate the quantification of water content using the systems and methods described herein, the following experiments were conducted.

The PANIR system described above and illustrated in FIGS. 1A, 1B, and 1C was used to quantify the water content in phantoms made of hydrogel. Hydrogel was used to construct the phantoms due to the similarity of the hydrogel's water content to that of typical connective tissues.

To prepare the hydrogel phantom, a beaker filled with a mixture of gelatin and distilled water was placed on a hot plate and heated to 90° C. A stir bar stirred the mixture at a constant speed. After the gelatin powder was completely dissolved in the mixture, the mixture was solidified in a Petri dish at room temperature (20° C.).

Figure 2A:
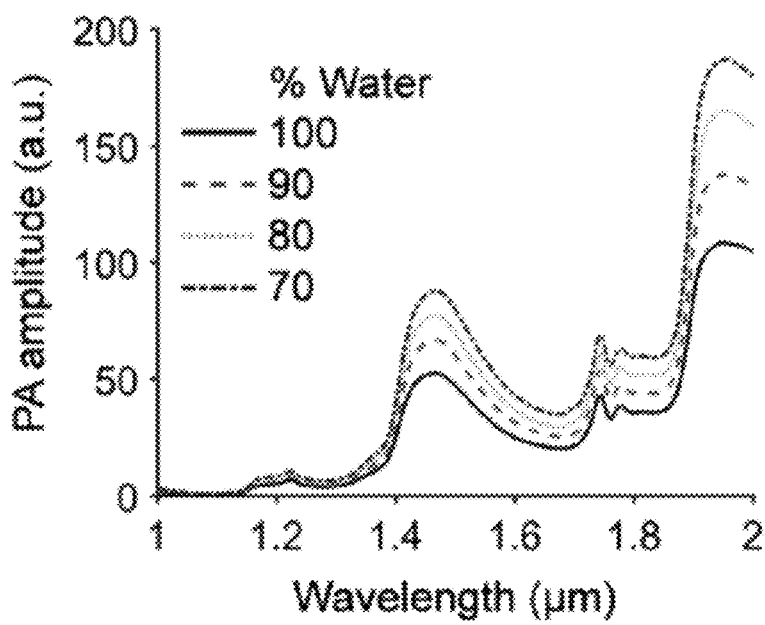
FIG. 2A is a graph of PANIR spectra measured from hydrogel phantoms made of water and gelatin containing several different water fractions.

The PANIR spectrum of the hydrogel phantom was obtained using the PANIR system described above. During data acquisition by the PANIR system, hydrogel phantom was maintained at 37.5° C. to mimic the temperature of the human cervix. The weight of the hydrogel phantom was recorded hourly to track changes in water content due to evaporation. FIG. 2A summarizes a family of PANIR spectra obtained from the hydrogel phantom with varying water content. As illustrated in FIG. 2A, the amplitude of the photoacoustic signals obtained from the hydrogel phantom increase the phantom's water content decreases, whereas the general profile of the PANIR spectra remained unchanged over the range of water content observed.

To quantify the water content in the hydrogel phantom, a single-wavelength linear regression model based on empirical calibration was fitted to the PANIR data. Single-wavelength models were used due to instabilities observed in multiwavelength models due to intercorrelation effects. To minimize any potentially confounding correlations between the PANIR measurements and any environmental variations, PANIR spectra were collected by random sample selection for both the calibration set and the validation set. The calibration set and the validation set each included 350 PANIR spectra measured from phantoms whose compositions covered a representative range of water contents in soft human tissues (70% to 100%). The single-wavelength linear regression model was fitted at two wavelengths: 1460 nm, corresponding to the first overtone of O—H stretching, and 1940 nm, corresponding to the second overtone of O—H stretching.

Figure 2B:
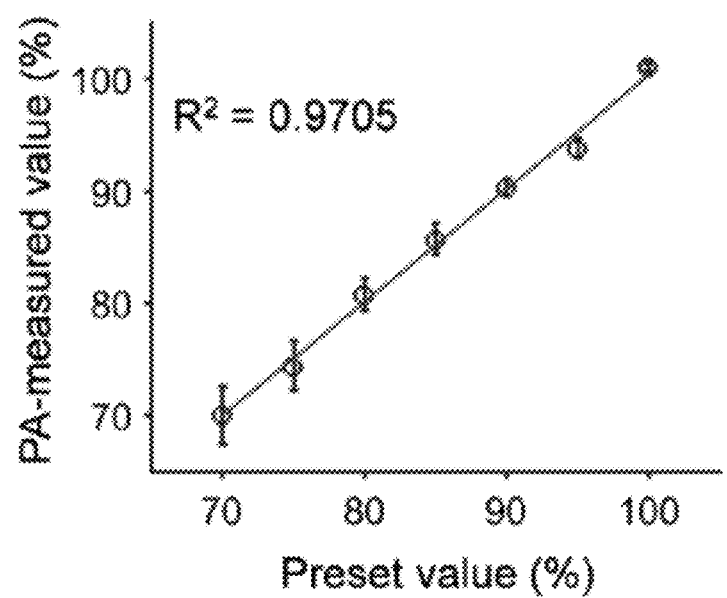
FIG. 2B is a graph comparing PA-measured phantom hydration to preset phantom hydration values expressed as percent water content. The preset phantom hydration values were obtained from measured weight loss due to water evaporation. The PA-measured phantom hydration values were obtained by fitting the PANIR spectra to a single-wavelength linear regression model at a wavelength of 1460 nm.
Figure 2C:
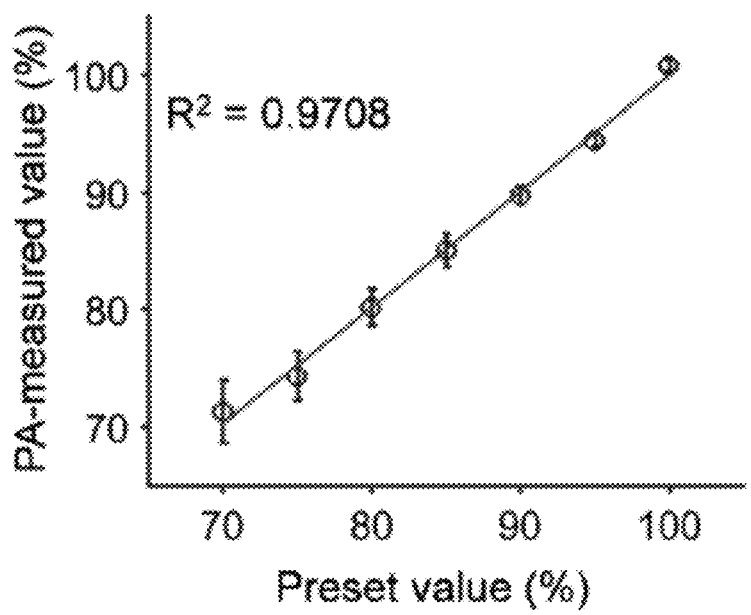
FIG. 2C is a graph comparing PA-measured phantom hydration to preset phantom hydration values expressed as percent water content. The preset phantom hydration values were obtained from measured weight loss due to water evaporation. The PA-measured phantom hydration values were obtained by subjecting the PANIR spectra to a single-wavelength linear regression model at a wavelength of 1940 nm.

Water contents of the hydrogel phantom were obtained using the PANIR measurements and single-wavelength linear regression models as described above. The PA-measured water contents were compared to the preset values obtained using serial weighing of the phantom. As summarized in FIGS. 2B and 2C, the measurements of water content agree with the preset values at wavelengths of 1460 nm and 1940 nm, respectively. As the water content in the hydrogel phantom decreased, the standard deviation of the measurements increased, because the gel network became more heterogeneous, causing local water content to fluctuate. At either wavelength, the single-wavelength linear regression model provided consistent and accurate predictions of water content.

Example 2: Effect of Photon Scattering on Quantification of Water Content

To assess the impact of photon scattering and attenuation typically associated with human cervical tissues on estimates of tissue water content using the PANIR systems and methods disclosed above, the following experiments were conducted.

Figure 3A:
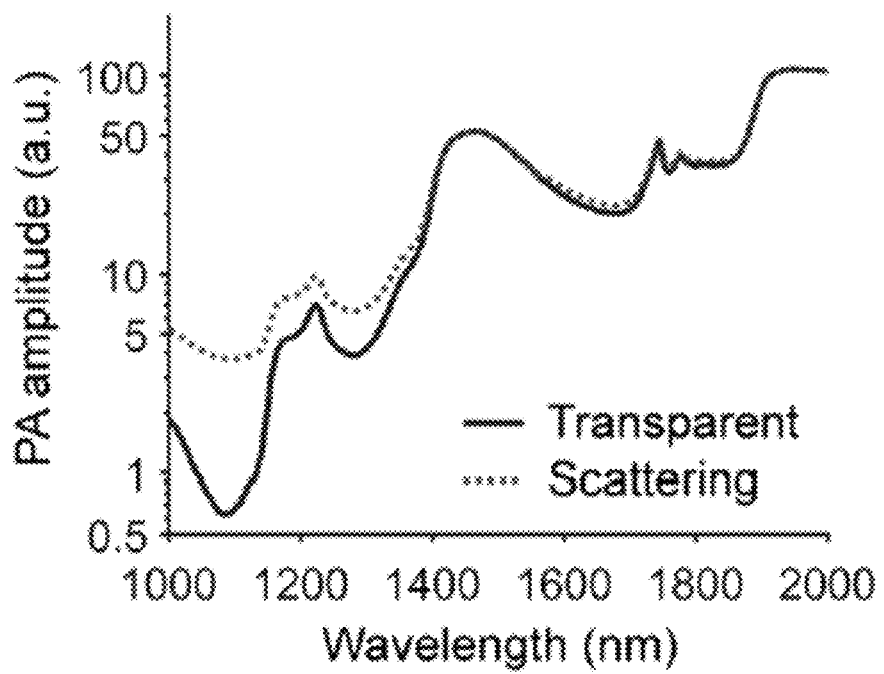
FIG. 3A is a graph illustrating the effect of photon scattering on PANIR spectra. The PANIR spectrum of distilled water (blue) was measured using the PANIR system and a Monte Carlo method was used to simulate the distortion of the measured PANIR spectra by scattering (red) to a degree comparable with the scattering observed in human skin.
Figure 3B:
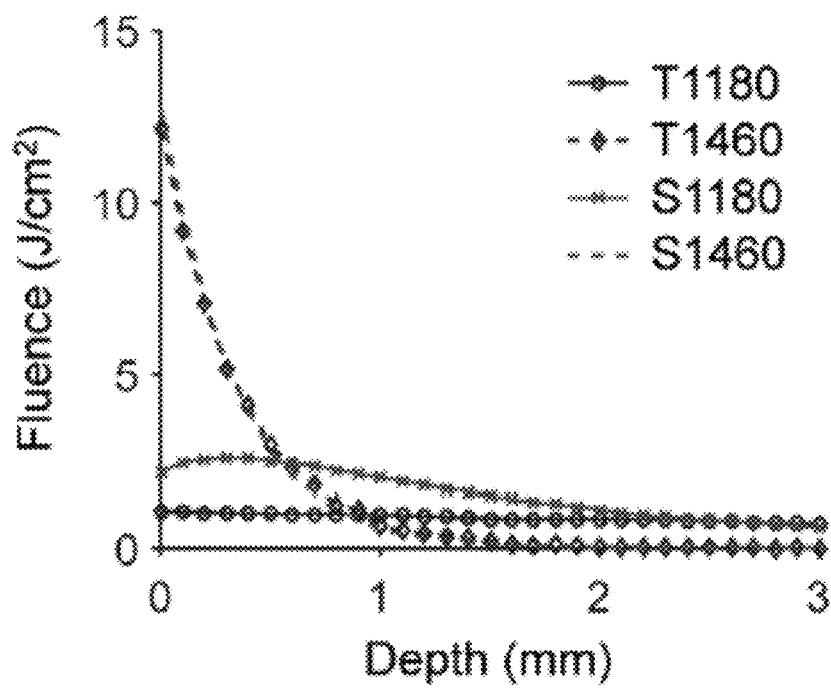
FIG. 3B is a graph summarizing the effects of scattering on the distributions of fluence in a medium. The absorption at 1460 nm is so strong that the scattering induces only a small perturbation of the distribution of fluence. Fluence simulations include: S1180, simulated at 1180 nm in the scattering medium; S1460, simulated at 1460 nm in the scattering medium; T1180, simulated at 1180 nm in the transparent medium; T1460, simulated at 1460 nm in the transparent medium. For illustrative purposes, T1460 and S1460 are divided by a factor of two.

For the measurement of water content in human cervical tissue using the PANIR system, scattering by the tissues may distort the PANIR spectrum measurements. To understand this influence, the hydrogel phantom measurements obtained in Ex. 1 were compared with results obtained using a Monte Carlo simulation that included optical properties representative of human tissue. FIG. 3A is a comparison of a PANIR spectrum obtained from distilled water (blue) and a PANIR spectrum distorted by Monte Carlo-simulated scattering comparable to human skin. As illustrated in FIG. 3A, at wavelengths ranging from about 1000 nm to about 1300 nm, the PA amplitudes of the PANIR spectrum with scattering were elevated relative to the PANIR spectrum of distilled water, likely because more photons were absorbed by water than transmitted due to scattering (see FIG. 3B). Within this wavelength range, the absorption coefficient ($\mu_a \geq 1$ cm$^{-1}$) is smaller than the reduced scattering coefficient ($\mu_s' \approx 12$ cm$^{-1}$). However, for the wavelengths at which the single-wavelength linear regression models were applied as described in Ex. 1 above (1460 nm and 1940 nm), where the absorption coefficient ($\mu_a$) is much larger than the reduced scattering coefficient ($\mu_s'$), the estimated impact of scattering on the PANIR spectrum was minimal. For example, at a wavelength of 1460 nm, the absorption coefficient $\mu_a$ is about 28 cm$^{-1}$ and the reduced scattering coefficient $\mu_s'$ is about 11 cm$^{-1}$, and as a result photon absorption by the tissue overwhelms the effects of scattering. Tissue scattering was predicted to have little influence on the PA amplitudes measured by the PANIR system for wavelengths in excess of about 1400, as illustrated in FIG. 3A.

The PANIR spectra of FIG. 3A were further processed using the single-wavelength linear regression models to obtain estimated water content as described in Ex. 1. Without correcting the PANIR spectrum for scattering, the water content of a scattering medium (SP) was slightly underestimated by about ~1%. This underestimation can be neglected as long as the typical change of water content in a physiological process is much >1%. In addition, the standard deviation of water contents caused by the cross-sectional change of scattering among the tissue samples was about one order smaller than the underestimation.

Figure 3C:
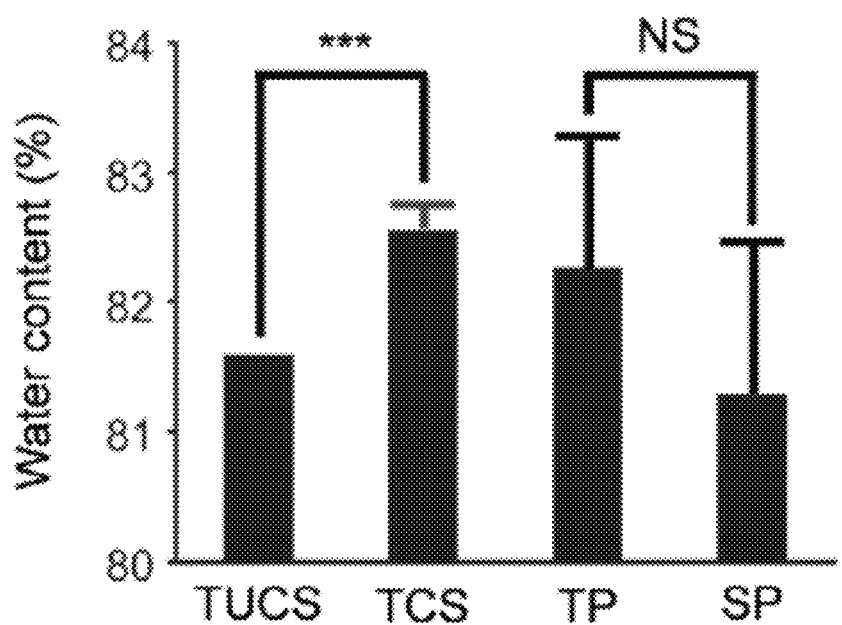
FIG. 3C is a graph summarizing the water contents of human tissue and hydrogel phantoms. The transparent model underestimates the water content of the scattering medium by ~1%. The red error bar and the black error bar, respectively, show the standard deviations contributed by the cross-sectional change of scattering among the tissue samples (n=16) and by the heterogeneity of the hydrogel phantoms (n=10). Data includes: SP, scattering phantom; TCS, tissue corrected for scattering; TP, transparent phantom; TUCS, tissue uncorrected for scattering. ***, $P<0.001$. NS, nonsignificant.

The minimal effect of scattering on PANIR-derived water contents as predicted by the Monte Carlo simulation described above (see FIG. 3A) was confirmed experimentally by comparing PANIR measurements of water content on a transparent phantom (hydro-gel with 18% gelatin) and on a scattering phantom (hydrogel with 1% Intralipid and 17% gelatin). As illustrated in FIG. 3C, the water content for the scattering phantom (SP) was about 1% lower than the corresponding water content of the transparent phantom (TP). The linear regression model underestimated the water content by ~1% in the scattering phantom relative to the transparent phantom, where the reduced scattering coefficient approximated the values used in the Monte Carlo simulation. This underestimation of water content in the scattering phantom was consistent with the results predicted by the Monte Carlo simulation results described above in FIG. 3A.

FIG. 3C further compares the water content measured from human tissue samples with no correction for scattering (TUCS) to the corresponding water content of the tissue samples corrected for scattering (TCS) using the results of the Monte Carlo simulation described above. The heterogenous gel networks of the phantoms resulted in larger standard deviations of water contents in the measurements (see black error bars in FIG. 3C), in comparison with the standard deviation associated with cross-sectional changes of scattering among the tissue samples (see red error bar in FIG. 3C). These results suggest that tissue scattering will have a minor effect, and that the heterogeneity of human tissue will dominate the variation of measured water contents in application.

Example 3: Quantification of Water Content in Human Cervical Connective Tissue

To validate the quantification of water content using the PANIR systems and methods described above, the following experiments were conducted. Serial and cross-sectional human studies were conducted to monitor the water content of human cervical connective tissue using the systems and methods described above.

Participants were recruited from a clinical patient population. Eligibility requirements included an age of 18 or older, the capability of informed consent, and a gestational age of <16 weeks. Exclusions included potential participants who were non-English speaking, unwilling to participate, carrying a twin pregnancy, or showing evidence of major fetal anomalies. Prior to measuring the cervix, the practitioner placed a speculum in the vagina, exposing the cervix for PANIR measurements. The PANIR spectrum obtained using the PANIR system as configured for these experiments had a spectral resolution of 5 nm, and each scan of one spectrum took about 10 seconds.

Analysis of the PANIR spectra obtained as described above was implemented as described in Ex. 1 and Ex. 2, based on the assumption that the photoacoustic and optical properties of the hydrogel phantoms and the cervical connective tissue sufficiently similar, such that the single-wavelength linear regression models derived in Ex. 1 and Ex. 2 were applicable to cervical connective tissue.

Figure 4A:
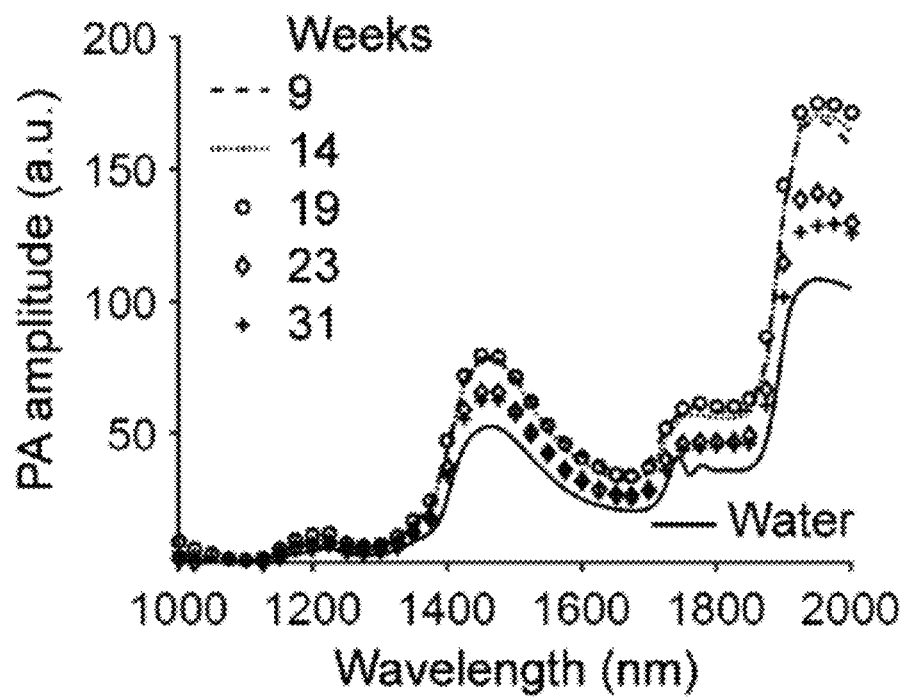
FIG. 4A is a graph of PANIR spectra measured from the cervix of a pregnant woman at five gestational time points.

FIG. 4A compares the PANIR spectra obtained from the cervical connective tissue of one pregnant woman at five gestational time points. As illustrated in FIG. 4A, the PANIR spectra of the cervix showed little change during the initial 20 weeks of gestation and subsequently dropped to lower levels at the end of the second trimester.

Figure 4B:
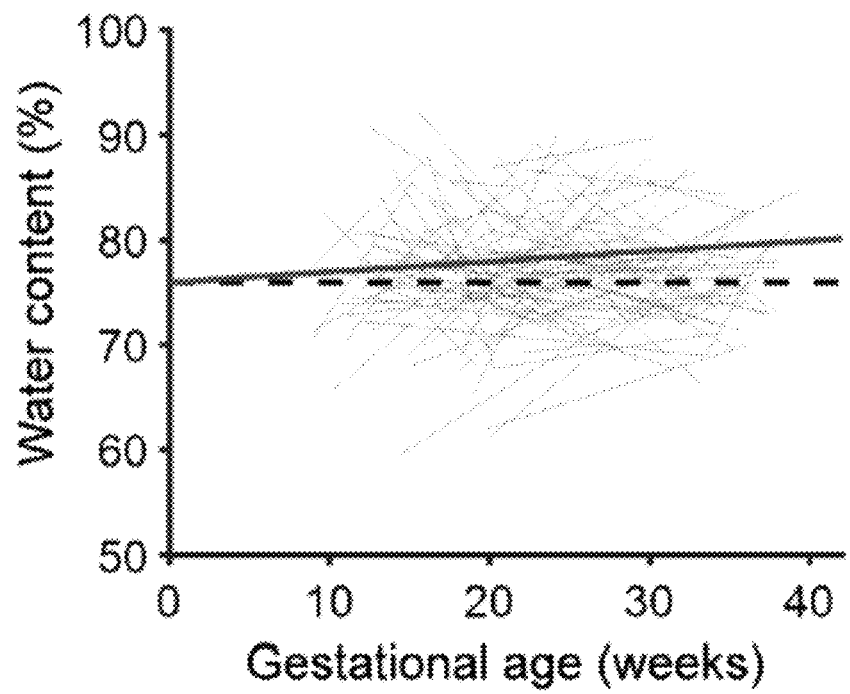
FIG. 4B is a graph showing longitudinal changes of water contents in the cervices of pregnant women (n=205), shown as gray lines. The red solid line indicates the fit at the unit level of the generalized linear model to the measured data. The black dashed line represents the level of intercept.

The PANIR spectra obtained from all participants were transformed into estimates of cervix water content using the single-wavelength linear regression models as described in Ex. 1 and Ex. 2. FIG. 4B is a graph showing the changes in cervical water content of all participants as grey lines. As illustrated in FIG. 4B, cervix water content typically increased overall with advancing gestational age of each participant. The individual trajectories of cervix water contents, however, were not the same for all participants. It is to be noted that the distribution of water contents calculated from the regression models described above were consistent with previously published biochemical data.

The cervical water content trajectories shown in FIG. 4B were subjected to a generalized linear model analysis to assess the linear association between gestational ages and cervical water contents. The data for each patient were grouped and modeled as the random components. The gestational age was defined as the irregularly spaced time variable. The results of the generalized linear analysis are summarized below in Table 1 and overlaid on the graph of FIG. 4B (red line). The slopes calculated in the generalized linear analysis (Table 1) indicated that the cervix water content had a significant linear effect with respect to gestational age.

TABLE 1

Results of the generalized linear model analysis.

|  | Value | Standard deviation | Degree of freedom | t-value | p-value |
|---|---|---|---|---|---|
| Intercept | 76.0 (%) | 1.1 (%) | 204 | 67.3 | 0 |
| Slope | 0.1 (%/week) | 0.1 (%/week) | 147 | 2.2 | 0.03 |

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

What is claimed is:

1. A photoacoustic endoscopic probe for obtaining photoacoustic near-infrared spectra from a region of interest, the probe comprising a pentaprism comprising a single optical-acoustic structure, the pentaprism comprising i) a beam combining face optically and acoustically coupled to the region of interest positioned outside the pentaprism, ii) an acoustic detection face acoustically coupled to an external acoustic detector, and iii) a light receiving face optically coupled to an external light source and defining an internal acoustically reflective face, wherein the pentaprism is configured to:
 a. receive light energy from the external light source into the pentaprism at the light receiving face;
 b. propagate the light energy internally through the pentaprism from the light receiving face to the beam combining face;
 c. direct the light energy out of the pentaprism through the beam combining face into the region of interest;
 d. receive photoacoustic signals generated by at least one structure within the region of interest into the pentaprism at the beam combining face, wherein the photoacoustic signals are produced within the region of interest in response to illumination by the light energy;
 e. propagate the photoacoustic signals internally through the pentaprism from the beam combining face to the internal acoustically reflective face;
 f. reflect the photoacoustic signals internally through the pentaprism toward the acoustic detection face; and
 g. direct the photoacoustic signals out of the pentaprism to the acoustic detector through the acoustic detection face.

2. The probe of claim 1, further comprising the acoustic detector coupled to the acoustic detecting face.

3. The probe of claim 2, wherein the acoustic detector comprises an acoustic transducer.

4. The probe of claim 3, further comprising at least one optical element configured to direct the light received from a multimode optical fiber coupled to the light source to the light receiving face of the pentaprism, wherein the at least one optical element comprises at least one of a plano-convex lens and a prism.

5. The probe of claim 4, wherein the light source is configured to produce the light in a wavelength scanning pattern ranging from a minimum wavelength to a maximum wavelength.

6. The probe of claim 5, wherein the minimum wavelength is 1000 nm and the maximum wavelength is 2000 nm.

7. The probe of claim 6, wherein the minimum wavelength is 1300 nm and the maximum wavelength is 2000 nm.

8. A method for measuring a hydration of a connective tissue in vivo using a photoacoustic endoscopic probe, the method comprising:
 a. providing a photoacoustic endoscopic probe, the photoacoustic endoscopic probe comprising a pentaprism, the pentaprism comprising) a beam combining face optically and acoustically coupled to the connective tissue positioned outside the pentaprism, ii) an acoustic detection face acoustically coupled to an external acoustic detector, and iii) a light receiving face optically coupled to an external light source and defining an internal acoustically reflective face;
 b. receiving the light energy from the external light source into the pentaprism at the light receiving face of the pentaprism, wherein the light energy is produced in a wavelength scanning pattern ranging from a minimum wavelength to a maximum wavelength;
 c. propagating the light energy internally through the pentaprism from the light receiving face to the beam combining face;
 d. directing the light energy out of the pentaprism through the beam combining face into the region of interest;
 e. receiving photoacoustic signals generated by at least one structure within the region of interest into the pentaprism at the beam combining face, wherein the photoacoustic signals are produced within the region of interest in response to illumination by the light energy;
 f. propagating the photoacoustic signals internally through the pentaprism from the beam combining face to the internal acoustically reflective face;
 g. reflecting the photoacoustic signals internally through the pentaprism from the internal acoustically reflective face toward the acoustic detection face; and
 h. directing the photoacoustic signals out of the pentaprism to the acoustic detector through the acoustic detection face;
 i. detecting, at the acoustic detector, the photoacoustic signals produced within the region of interest in respond to illumination by the light energy;
 j. transforming the detected photoacoustic signals into a photoacoustic spectrum, the photoacoustic spectrum comprising a plurality of photoacoustic signals and a corresponding wavelength, the corresponding wavelength indicative of the wavelength of light used to produce the corresponding photoacoustic signal; and
 k. transforming the photoacoustic spectrum into the hydration of the connective tissue using at least one predetermined single wavelength linear regression model.

* * * * *